US010085868B2

(12) United States Patent
Kitano et al.

(10) Patent No.: US 10,085,868 B2
(45) Date of Patent: Oct. 2, 2018

(54) BOWLEG CORRECTION DEVICE

(71) Applicant: OSMOTIC JAPAN Co., Ltd, Mitoyo-shi (JP)

(72) Inventors: Yuki Kitano, Mitoyo (JP); Hiroyuki Matsuura, Zentsuji (JP); Nobuyuki Matsukuma, Kasuya-gun (JP)

(73) Assignee: OSMOTIC JAPAN CO., LTD, Mitoyo-Shi (JP)

( * ) Notice: Subject to any disclaimer, the term of this patent is extended or adjusted under 35 U.S.C. 154(b) by 372 days.

(21) Appl. No.: 15/082,045

(22) Filed: Mar. 28, 2016

(65) Prior Publication Data

US 2016/0235570 A1    Aug. 18, 2016

Related U.S. Application Data

(63) Continuation of application No. PCT/JP2015/079392, filed on Oct. 13, 2015.

(30) Foreign Application Priority Data

Oct. 17, 2014    (JP) .................... 2014-212146

(51) Int. Cl.
  *A61F 5/01*      (2006.01)
  *A63B 23/08*     (2006.01)
  *A63B 21/068*    (2006.01)
  *A63B 22/14*     (2006.01)
  *A63B 22/18*     (2006.01)
  *A63B 23/035*    (2006.01)
    (Continued)

(52) U.S. Cl.
  CPC .......... *A61F 5/0102* (2013.01); *A63B 21/068* (2013.01); *A63B 21/4015* (2015.10); *A63B 21/4025* (2015.10); *A63B 22/14* (2013.01); *A63B 22/18* (2013.01); *A63B 23/03508* (2013.01); *A63B 23/08* (2013.01); *A63B 2026/006* (2013.01)

(58) Field of Classification Search
  CPC ............... A61F 5/0102; A63B 21/4025; A63B 21/4015; A63B 23/03508; A63B 22/14; A63B 21/068; A63B 22/18; A63B 23/08; A63B 2026/006
  USPC .......................................... 602/25
  See application file for complete search history.

(56) References Cited

FOREIGN PATENT DOCUMENTS

| JP | 1998-73035   | 3/1998 |
| JP | 2003-047672  | 2/2003 |
| JP | 2009-125557  | 6/2009 |

(Continued)

*Primary Examiner* — Tarla Patel
(74) *Attorney, Agent, or Firm* — Lex IP Meister, PLLC

(57) ABSTRACT

A bowleg correction device 1 includes a pair of left and right foot mounting units 10 configured to respectively mount user feet from upper surface sides thereof; and rotating portions 20 respectively fixed to the foot mounting units 10, each of which has at least a part protruded from a lower surface side of the corresponding foot mounting unit 10, wherein each of the rotating portions 20 includes: a fixed portion 21 fixed to the corresponding foot mounting unit 10; and a shaft portion 22 rotatably engaged with the fixed portion 21, extending in a vertical direction and having a floor-contacting surface 22a which contacts a floor at a position that is protruded from a bottom surface 12a of the foot mounting unit 10, and when the foot mounting unit 10 is rotated around the shaft portion 22 in a direction, a returning force is generated in the opposite direction.

2 Claims, 8 Drawing Sheets

(51) Int. Cl.
     *A63B 21/00*      (2006.01)
     *A63B 26/00*      (2006.01)

(56)      References Cited

FOREIGN PATENT DOCUMENTS

| | | | |
|---|---|---|---|
| JP | 2013220261 A | * | 10/2013 |
| JP | 2014-113182 | | 6/2014 |
| KP | 2003-47672 | | 2/2003 |

* cited by examiner

US 10,085,868 B2

BOWLEG CORRECTION DEVICE

TECHNICAL FIELD

The present invention relates to a bowleg correction device, and more particularly to a bowleg correction device installed on a floor to perform training for correcting bowlegs.

DESCRIPTION OF THE RELATED ART

Conventionally, when a gap is formed between both knees in a standing posture with both tiptoes and heels together, this condition is diagnosed with bowlegs. The bowlegs comes from an increased distance between both knees caused by inward rotation of the knees owing to inward rotation of femurs of both legs. Hence, the training for lateral rotator muscles of coxa makes it possible to maintain the knees to a normal state by outwardly rotating both legs with a force of the lateral rotator muscles. As a result, the bowlegs can be corrected.

To that end, Patent Document 1 suggests a bowleg correcting device including: a pair of foot orthoses which are respectively put on both feet of a user; and a toe side connection member which connects toe parts of the foot orthoses to each other. The toe side connection member is configured to be elastically extensible and contractible by rotating the foot orthoses around a heel part.

This bowleg correcting device can facilitate effective bowlegs correction by enabling the user to do easy and effective training.

[Patent Document 1]
Japanese Patent Application Publication No. 2014-113182

SUMMARY

However, it is preferable to carry out the training for correcting bowlegs continuously. For this reason, it is required to provide a bowleg correction device capable of quick start and easy to locate for effective training.

The present invention has been made in an effort to provide a bowleg correction device which is compact and enables quick start of effective training.

According to a first aspect of the present invention, a bowleg correction device installed on a floor to perform a training for correcting bowlegs includes a pair of left and right foot mounting units configured to respectively mount user feet from upper surface side thereof; and rotating portions respectively fixed to the foot mounting units and having at least a part protruded from lower surface of the foot mounting units, wherein each of the rotating portions includes: a fixed portion fixed to the corresponding foot mounting unit; and a shaft portion rotatably engaged with the fixed portion, extending in a vertical direction and having a floor-contacting surface which contacts the floor at a position that is protruded from the lower surface of the foot mounting unit, and when the foot mounting unit is rotated around the shaft portion in a first direction, a returning force is generated in a second direction that is opposite to the first direction. According to the aspect of the present invention, the bowleg correction device is installed on the floor to serve to perform a training for correcting bowlegs, and includes the pair of left and right foot mounting units and the rotating portions. The user feet are respectively mounted in the left and right mounting units from the upper surface side thereof. The rotating portions are respectively fixed to the foot mounting units, each of which has at least a part protruded from the lower surface of the corresponding foot mounting unit. The fixed portion is fixed to the corresponding foot mounting unit. The shaft portion is rotatably engaged with the fixed portion and extends in the vertical direction. The shaft portion has a floor-contacting surface which contacts the floor at a position that is protruded from the lower surface of the foot mounting unit. In addition, when the foot mounting unit is rotated around the shaft portion in a first direction, a returning force is generated in a second direction that is opposite to the first direction.

According to the bowleg correction device, each of the left part and the right part is configured to include the foot mounting unit for mounting a corresponding foot of the user and the rotating portion protruded from the lower surface side of the foot mounting unit. Accordingly, it is possible to make the device compacter than a device, for example, having a member rotatably supporting a pair of foot mounting units together. Further, when the user respectively mounts both feet in the left and right foot mounting units and rotates the foot mounting units to open a toe side by using lateral rotator muscles, a returning force is generated in a direction of closing the toe side in the fixed portion, thereby enabling effective training. In addition, the user can start the training by simply mounting both feet in the left and right foot mounting units of the bowleg correction device installed on the floor. Accordingly, it is possible to provide a bowleg correction device compact and enabling quick start of effective training.

According to a second aspect of the present invention, the rotating portion further includes a spring that is extended in a vertical direction, and the spring is configured to have an upper end that is fixed to the fixed portion and a lower end that is fixed to the shaft portion.

According to the second aspect of the present invention, when the user respectively mounts both feet in the left and right foot mounting units and rotates the foot mounting units to open the toe side, a pressure is applied in a direction of closing the toe side by the spring, thereby enabling effective training.

According to a third aspect of the present invention, the fixed portion has a cylindrically shaped inner wall having an external circumferential surface on which a spiral fixed portion groove is formed, the shaft portion has a cylindrically shaped outer wall having an inner diameter that is slightly larger than an outer diameter of the inner wall and an interior circumferential surface on which a shaft portion groove having a same shape as the fixed portion groove is formed, and the rotating portion further includes a bearing disposed between the fixed portion groove and the shaft portion groove.

According to a third aspect of the present invention, when the fixed portion is rotated in a predetermined direction, the bearing disposed between the fixed portion groove and the shaft portion groove of the shaft portion is rotated, and is upwardly moved along the spiral shaft portion groove of the shaft portion.

As such, when the user respectively mounts both feet in the left and right foot mounting units and rotates the foot mounting units to open the toe side, the fixed portions fixed to the foot mounting units are respectively upwardly moved along the spiral shaft portion grooves of the shaft portions. In this case, a downwardly directed force caused by a user weight works as a rotating force in a direction of closing the toe side by the action of the fixed portion grooves of the fixed portions, the shaft portion grooves of the shaft portions, and the bearings disposed therebetween. As a result, the rotating force in the direction of closing the toe side caused by the user weight is generated in the foot mounting units.

As such, it is possible to apply a load in the same direction as the spring to the foot mounting units by spirally rotating the fixed portion fixed to each of the foot mounting units through a structure which includes the fixed portion groove, the shaft portion groove, and the bearing to rise above while rotating. In addition, since the bearing is less deteriorated than the spring, it is possible to use the bowleg correction device for a long time.

According to the present invention, it is possible to provide a bowleg correction device compact and enabling quick start of effective training

DETAILED DESCRIPTION OF THE EMBODIMENTS

Figure 1:
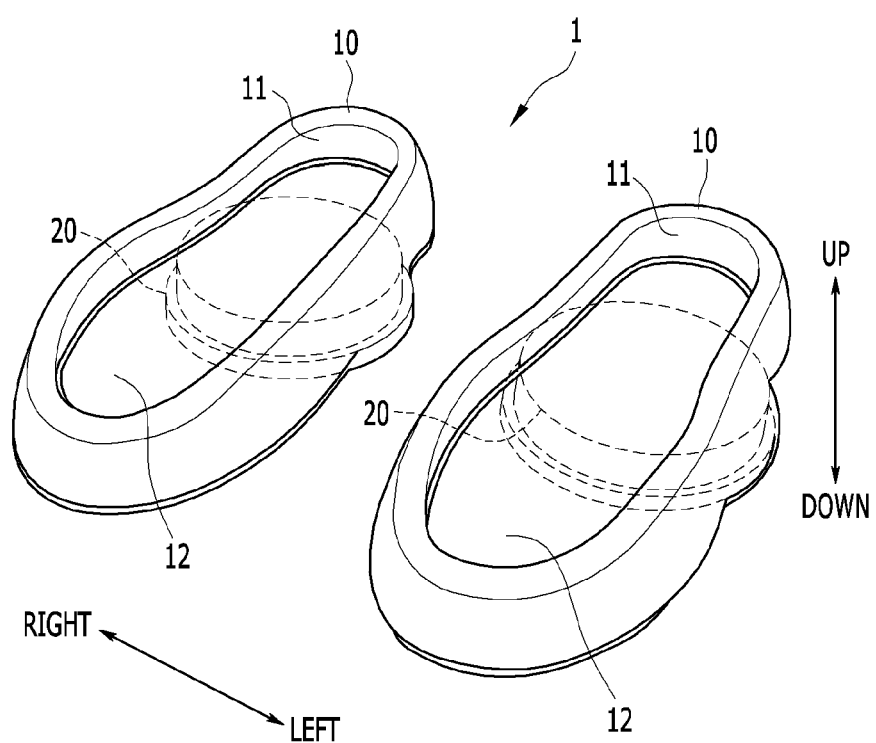
FIG. 1 is a perspective view illustrating a bowleg correction device 1 according to a first exemplary embodiment of the present invention.

Hereinafter, exemplary embodiments of the present invention will be described with reference to the drawings. In the description below, same reference numerals designate same elements to omit or simplify the description thereof.

First Exemplary Embodiment

FIG. 1 is a perspective view illustrating a bowleg correction device 1 according to a first exemplary embodiment of the present invention.

The bowleg correction device 1 which is installed on a floor serves to perform a training for correcting bowlegs, and includes a pair of left and right foot mounting units 10 and a rotating portion 20 attached to each of the foot mounting units 10.

In the foot mounting units 10, feet of a user are mounted from upper surface sides thereof. Specifically, each of the foot mounting units 10 in which the user feet are mounted from the upper surface sides includes a foot accommodating portion 11 serving as a hole having an appearance that is slightly larger than that of a foot of the user, and a sole portion 12 disposed below the foot accommodating portion 11 and attached to a rotating portion 20.

Figure 2:
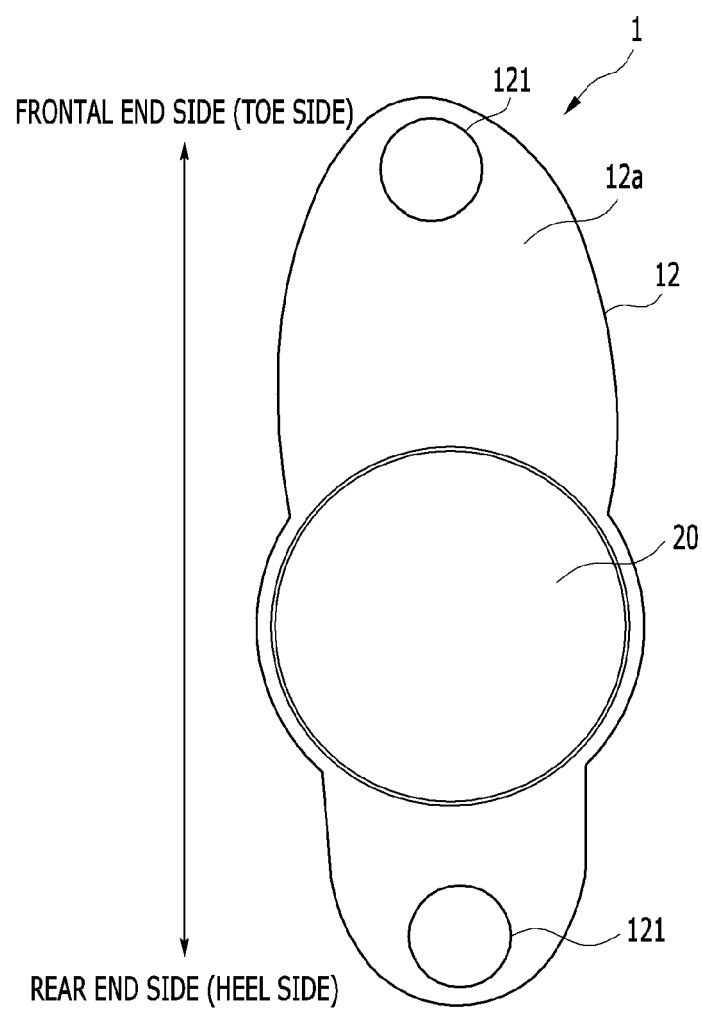
FIG. 2 is a bottom view illustrating the bowleg correction device 1 according to the first exemplary embodiment of the present invention.

FIG. 2 is a bottom view illustrating the bowleg correction device 1 according to the first exemplary embodiment of the present invention.

Figure 3:
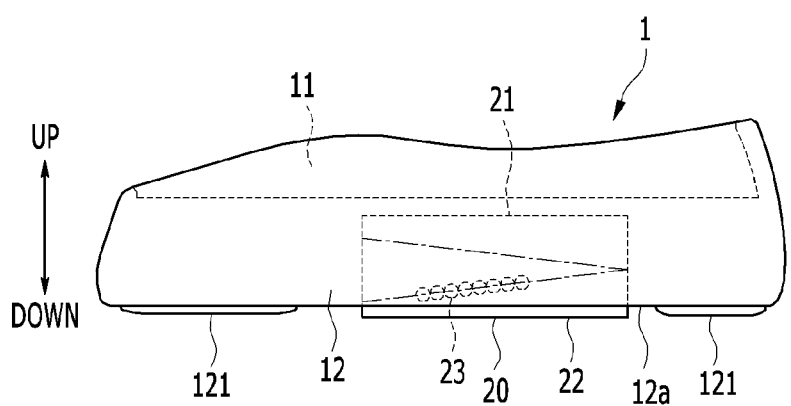
FIG. 3 is a side view illustrating the bowleg correction device 1 according to the first exemplary embodiment of the present invention.

FIG. 3 is a side view illustrating the bowleg correction device 1 according to the first exemplary embodiment of the present invention.

In FIG. 2 and FIG. 3, a left foot side of the bowleg correction device 1 is illustrated. A right foot side of the bowleg correction device 1 has the same configuration as that of the left foot side thereof except that the right foot side is bilaterally symmetrical to the left foot side, and thus a drawing and a description related thereto will be omitted.

In the sole portion 12, a slip seat 121 having a smooth surface is provided at a frontal end side (toe side when a user foot is placed) and a rear end side (heel side when the user foot is placed) of a bottom surface 12a thereof.

Details will be described later. As shown in FIG. 3, a part of the rotating portion 20 is protruded from the bottom surface 12a of the sole portion 12. The slip seat 121 is formed to have a thickness that is thinner than that of the protruded part of the rotating portion 20, and an edge of the slip seat 121 is chamfered.

As shown in FIG. 3, the rotating portion 20 is fixed to the foot mounting unit 10, and at least a part thereof is protruded from the bottom surface 12a which is a lower surface of the foot mounting unit 10. The rotating portion 20 includes a fixed portion 21, a shaft portion 22, and a bearing 23.

The fixed portion 21 is fixed to the sole portion 12 of the foot mounting unit 10.

Figure 4:
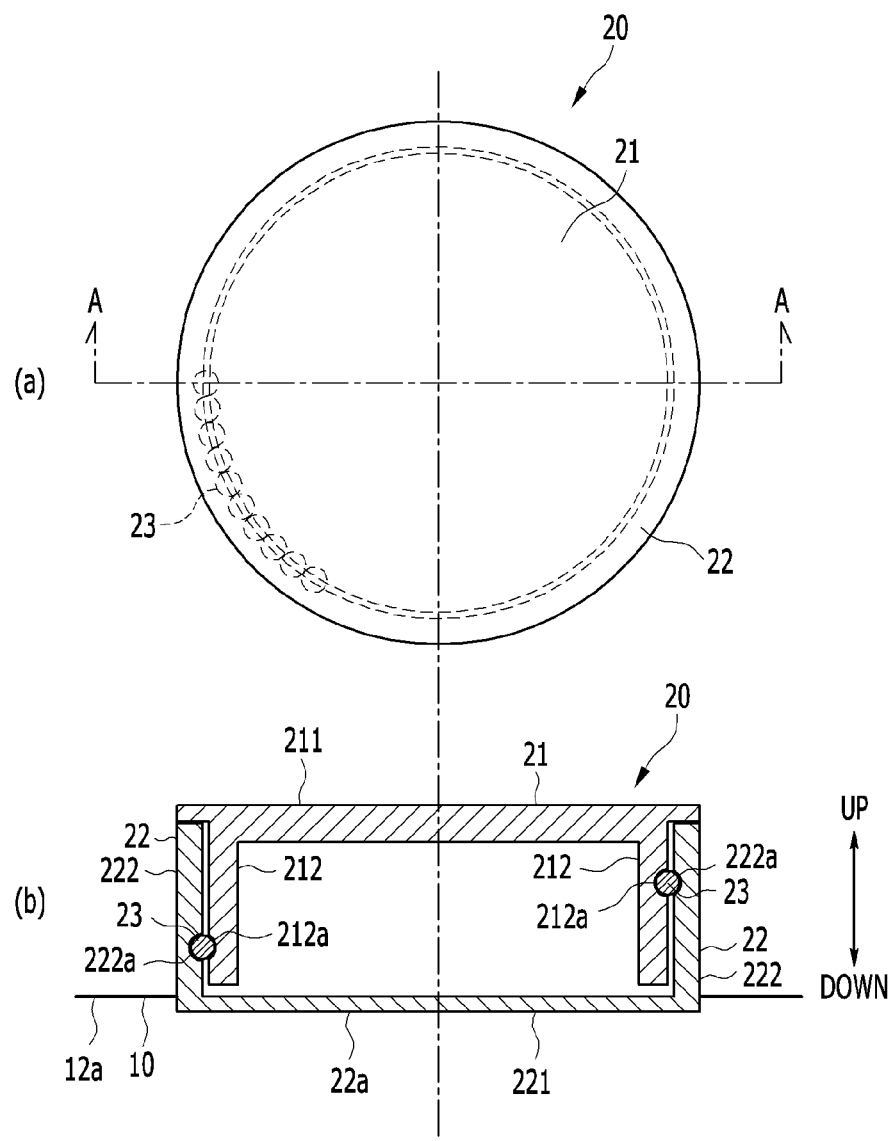
FIG. 4 illustrates a rotating portion 20 according to the first exemplary embodiment of the present invention. Part (a) is a top plan view of the rotating portion 20. Part (b) is a cross-sectional view of the rotating portion 20 taken along a line A-A.

FIG. 4 illustrates a rotating portion 20 according to the first exemplary embodiment of the present invention. Part (a) is a top plan view of the rotating portion 20. Part (b) is a cross-sectional view of the rotating portion 20 taken along a line A-A.

The shaft portion 22 is rotatably engaged with the fixed portion 21 to extend in a vertical direction, and has a floor-contacting surface 22a at a position that is protruded from the bottom surface 12a of the foot mounting unit 10. The floor-contacting surface 22a contact the floor.

Specifically, as shown in part (b) of FIG. 4, the fixed portion 21 supports the foot mounting unit 10 on an upper surface thereof and includes a top plate portion 211 formed in a disk shape and an inner wall portion 212 formed in a cylindrical shape downwardly extending from a lower surface of the top plate portion 211. A spiral fixed portion groove 212a is formed on an external circumferential surface of the inner wall portion 212.

The shaft portion 22 includes a bottom plate 221 having the floor-contacting surface 22a that contacts the floor, and an outer wall portion 222 formed to be upwardly erect from an outer edge of the bottom plate 221 in a cylindrical shape having an inner diameter that is slightly larger than an outer diameter of the inner wall portion 212 of the fixed portion 21. A shaft portion groove 222a having the same shape as the fixed portion groove 212a is formed on an interior circumferential surface of the outer wall portion 222.

Dotted lines shown in part (a) of FIG. 4 indicate trajectories of the fixed portion groove 212a of the fixed portion 21 and the shaft portion groove 222a of the shaft portion 22.

The bearings 23 are a plurality of spheres disposed between the fixed portion groove 212a and the shaft portion groove 222a. Further, in FIG. 3 and FIG. 4, the spheres are partly illustrated, but the spheres are arranged in an entire length of the fixed portion groove 212a.

Next, an operation of the bowleg correction device 1 according to the first exemplary embodiment will be described.

Figure 5:
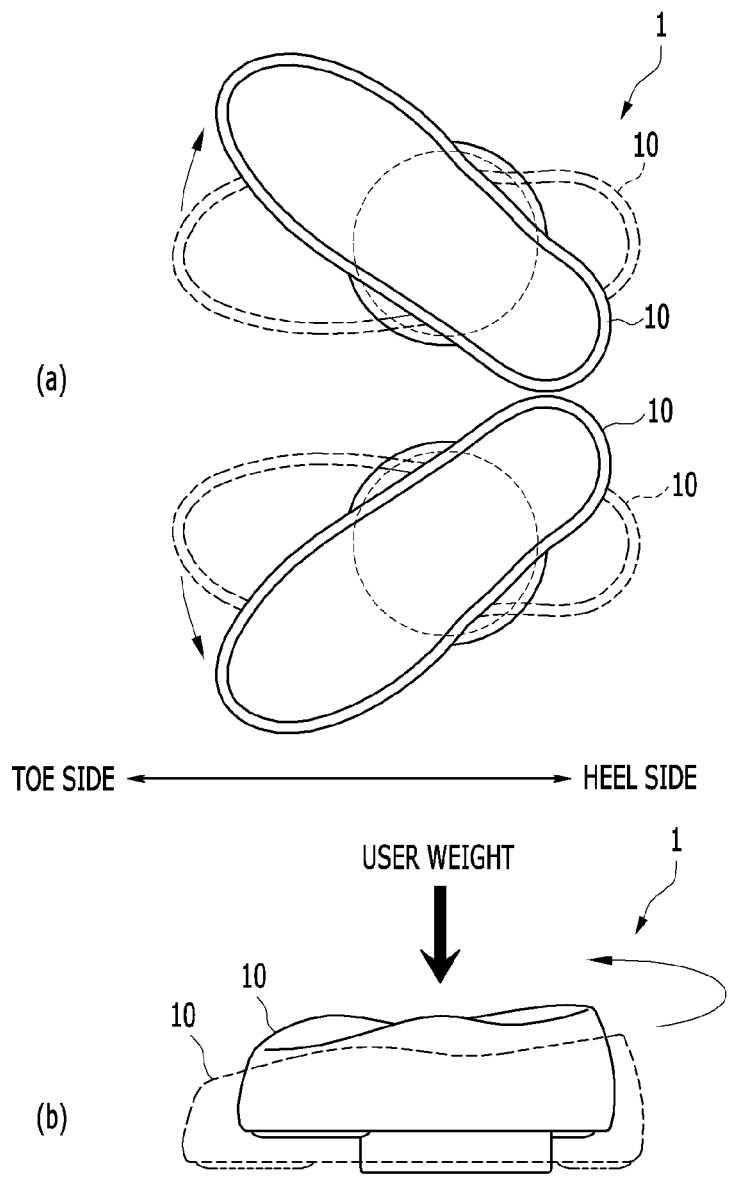
FIG. 5 illustrate an operation of the bowleg correction device 1 according to the first exemplary embodiment of the present invention. Part (a) is a top plan view of the bowleg correction device 1. Part (b) is a side view of the bowleg correction device 1.

FIG. 5 illustrate an operation of the bowleg correction device 1 according to the first exemplary embodiment of the present invention. Part (a) is a top plan view of the bowleg correction device 1. Part (b) is a side view of the bowleg correction device 1.

A user mounts both feet respectively in the pair of left and right foot mounting units 10, and rotates the foot mounting units 10 from dotted-line positions to solid-line positions shown in FIG. 5 to open a toe side. Accordingly, a returning force is generated in an opposite direction to the direction in which the toe side is opened in the foot mounting units 10.

Specifically, when the user mounts the feet respectively in the left and right foot mounting units 10 and rotates the foot mounting units 10 to open the toe side, the fixed portion 21 (see FIG. 4) fixed to each of the foot mounting units 10 is rotated and is upwardly moved along the spiral shaft portion groove 222a (see FIG. 4) of the shaft portion 22 (see FIG. 4). In this case, a downwardly directed force caused by a user weight works as a rotating force in a direction of closing the toe side by the action of the fixed portion groove 212a (see FIG. 4) of the fixed portion 21, the shaft portion groove 222a of the shaft portion 22, and the bearings 23 (see FIG. 4) disposed therebetween. As a result, the rotating force in the direction of closing the toe side caused by the user weight is generated in the foot mounting units 10.

According to the first exemplary embodiment, it is possible to apply a load such as a spring to the foot mounting units 10 by spirally rotating the fixed portion 21 fixed to each of the foot mounting units 10 through a structure which includes the fixed portion groove 212a, the shaft portion groove 222a, and the bearings 23 to rise above while rotating. In addition, since the bearing 23 is less deteriorated than a spring, it is possible to enhance a durability of the bowleg correction device 1.

Second Exemplary Embodiment

Next, a bowleg correction device 1A according to a second exemplary embodiment of the present invention will be described.

The bowleg correction device 1A of the second exemplary embodiment is mainly different from the bowleg correction device 1 of the first exemplary embodiment in a configuration of rotating portion 20A.

Figure 6:
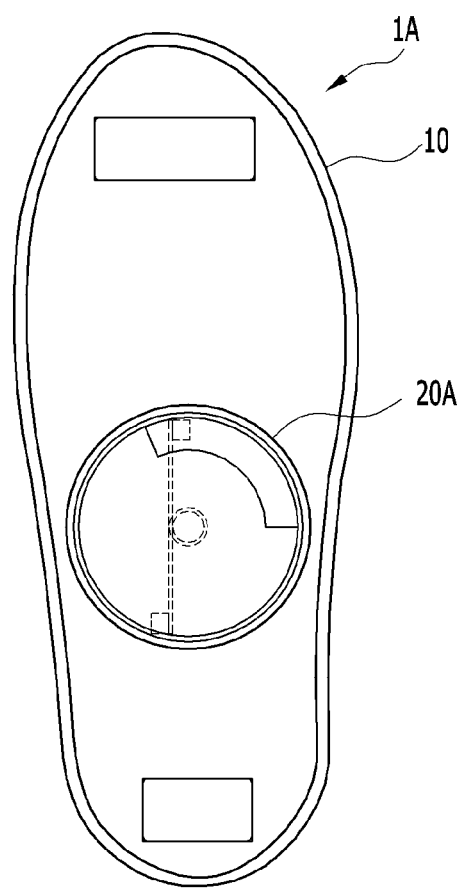
FIG. 6 is a bottom view illustrating a bowleg correction device 1A according to a second exemplary embodiment of the present invention.

FIG. 6 is a bottom view illustrating a bowleg correction device 1A according to a second exemplary embodiment of the present invention.

Figure 7:
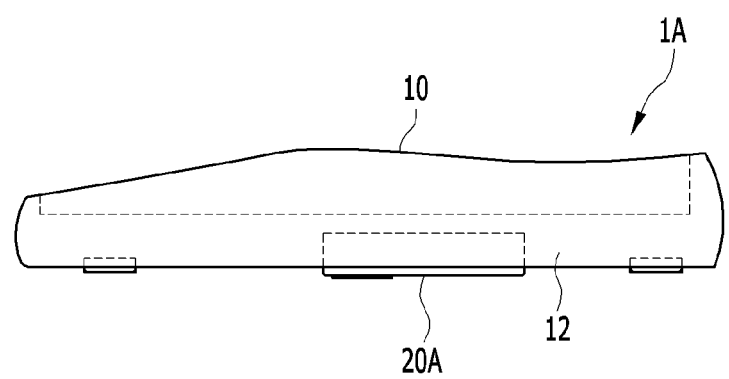
FIG. 7 is a side view illustrating the bowleg correction device 1A according to the second exemplary embodiment of the present invention.

FIG. 7 is a side view illustrating the bowleg correction device 1A according to the second exemplary embodiment of the present invention.

In FIG. 6 and FIG. 7, a left foot side of the bowleg correction device 1A is illustrated. A right foot side of the bowleg correction device 1A has the same configuration as that of the left foot side thereof except that the right foot side is bilaterally symmetrical with the left foot side, and thus a drawing and a description related thereto will be omitted.

The bowleg correction device 1A which is installed on a floor serves to perform a training for correcting bowlegs, and includes a pair of left and right foot mounting units 10 and rotating portions 20A attached to each of the foot mounting units 10.

Figure 8:
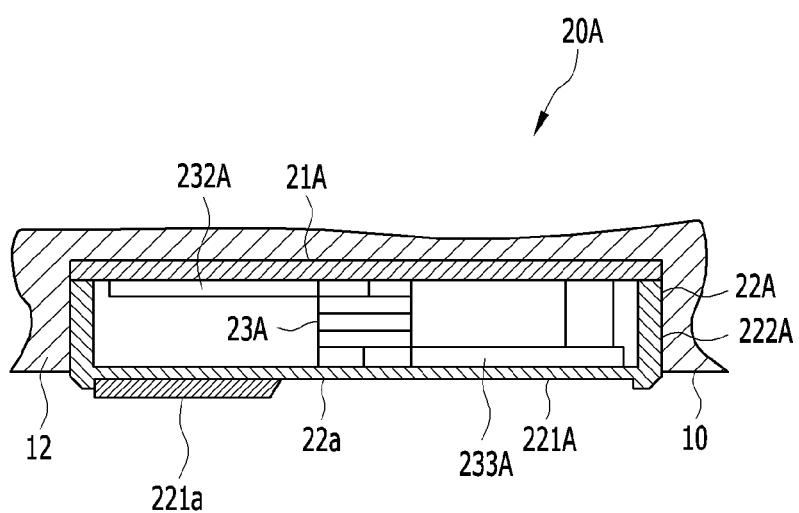
FIG. 8 is a cross-sectional view illustrating a rotating portion 20A according to the second exemplary embodiment of the present invention.

FIG. 8 is a cross-sectional view illustrating the rotating portion 20A according to the second exemplary embodiment of the present invention.

The rotating portion 20A is fixed to the foot mounting unit 10, and a part thereof is protruded from the bottom surface 12a which is a lower surface of the foot mounting unit 10. The rotating portion 20A includes a fixed portion 21A, a shaft portion 22A, and a spring 23A.

The fixed portion 21A is formed in a disk shape to have an upper surface that is fixed to the sole portion 12 and a lower surface to which the spring 23A is coupled.

The shaft portion 22A includes a bottom plate 221A having a floor-contacting surface 22a that contacts the floor, and an outer wall portion 222A formed to be upwardly erect from an outer edge of the bottom plate 221A in a cylindrical shape having an inner diameter that is substantially the same as an outer diameter of the fixed portion 21. The spring 23A is disposed at inside of the outer wall portion 222A.

The bottom plate 221A includes a rubber plate 221a on the floor-contact surface 22a to prevent slipping.

The spring 23A includes a spring main body 231 A disposed at a center of the shaft portion 22A, a portion supporter 232A extended in a horizontal direction from an upper end of the spring main body 231A to be fixed to the fixed portion 21A, and a shaft portion supporter 233A extended in the horizontal direction from a lower end of the spring main body 231A to be fixed to the shaft portion 22A.

According to the bowleg correction device 1A of the second exemplary embodiment, when a user respectively mounts both feet in the foot mounting units 10 and rotates the foot mounting units 10 to open a toe side, the fixed portions 21A fixed to the foot mounting units 10 are respectively rotated around the shaft portions 22A which contact the floor. Then, a pressure is applied in a direction of closing the toe side by the spring 23A fixed to the fixed portion 21A, thereby enabling effective training.

As described above, according to the bowleg correction device 1 of the first exemplary embodiment and the bowleg correction device 1A of the second exemplary embodiment, each of the left part and the right part is configured to include the foot mounting unit 10 for mounting a corresponding foot of the user and the rotating portion 20 or 20A protruded from the lower surface of the foot mounting unit 10. Accordingly, it is possible to make the bowleg correction device 1 compacter than a device in which a member for rotatably supporting the pair of foot mounting units together is installed.

Further, when the user respectively mounts both feet in the left and right foot mounting units 10 and rotates the foot mounting units 10 to open a toe side by using lateral rotator muscles, a returning force is generated in a direction of closing the toe side in the fixed portion 21 or 21A, thereby enabling effective training.

In addition, the user can start the training by simply mounting both feet in the left and right foot mounting units 10 of the bowleg correction device 1 or 1A installed on the floor.

Accordingly, it is possible to provide a bowleg correction device compact and enabling quick start of effective training.

The present invention is not limited to the first exemplary embodiment and the second exemplary embodiment, but is intended to cover various modifications and equivalent arrangements included within the spirit and scope of the appended claims.

DESCRIPTION OF SYMBOLS 1, 1A; bowleg correction device
10; foot mounting unit

11; foot accommodating portion
12; sole portion
12a; bottom surface
121; sheet
20, 20A; rotating portion
21, 21A; fixed portion
211; top plate portion
212; inner wall portion
212a; fixed portion groove
22, 22A; shaft portion
22A; shaft portion
22a; floor-contacting surface
221, 221A; bottom plate
221a; rubber plate
222; outer wall portion
222A; outer wall portion
222a; shaft portion groove
23; bearing
23A; spring
231A; spring main body
232A; fixed portion supporter
233A; shaft portion supporter

What is claimed is:

1. A bowleg correction device installed on a floor to perform a training for correcting bowlegs, the bowleg correction device comprising:
    a pair of left and right foot mounting units configured to respectively mount user feet from upper surface sides thereof; and
    a pair of rotating portions respectively fixed to the left and right foot mounting units, each of which has at least a part protruded from a lower surface of the corresponding foot mounting unit,
    wherein each of the left and right rotating portion include:
    a fixed portion fixed to the corresponding foot mounting unit;
    a shaft portion rotatably engaged with the fixed portion, extending in a vertical direction and having a floor-contacting surface which contacts the floor at a position that is protruded from the lower surface of the foot mounting unit; and
    a spring extended in a vertical direction to have an upper end that is fixed to the fixed portion and a lower end that is fixed to the shaft portion,
    wherein the spring includes a spring main body disposed at a center of the shaft portion, a fixed portion supporter extended in a horizontal direction from an upper end of the spring main body to be fixed to the fixed portion, and a shaft portion supporter extended in the horizontal direction from a lower end of the spring main body to be fixed to the shaft portion, and
    when the foot mounting units in which both feet are respectively mounted are rotated to open a toe side, the fixed portions fixed to the foot mounting units are respectively rotated around the shaft portions which contact the floor, and a pressure is applied in a direction of closing the toe side by the springs fixed to the fixed portions.

2. The bowleg correction device of claim 1, wherein the fixed portion has a cylindrically shaped inner wall having an external circumferential surface on which a spiral fixed portion groove is formed,
    the shaft portion has a cylindrically shaped outer wall having an inner diameter that is slightly larger than an outer diameter of the inner wall and an interior circumferential surface on which a shaft portion groove having a same shape as the fixed portion groove is formed, and
    the rotating portion further comprises a bearing disposed between the fixed portion groove and the shaft portion groove.

* * * * *